(12) United States Patent
Krauss

(10) Patent No.: US 8,068,578 B2
(45) Date of Patent: Nov. 29, 2011

(54) METHOD FOR RECOGNIZING AND MARKING CONTRAST AGENTS IN BLOOD VESSELS OF THE LUNG WITH THE AID OF A CT EXAMINATION AND AN IMAGE EVALUATION UNIT OF A CT SYSTEM

(75) Inventor: Bernhard Krauss, Altdorf (DE)

(73) Assignee: Siemens Aktiengesellschaft, Munich (DE)

( * ) Notice: Subject to any disclaimer, the term of this patent is extended or adjusted under 35 U.S.C. 154(b) by 155 days.

(21) Appl. No.: 12/232,523

(22) Filed: Sep. 18, 2008

(65) Prior Publication Data

US 2009/0086884 A1 Apr. 2, 2009

(30) Foreign Application Priority Data

Sep. 28, 2007 (DE) .......................... 10 2007 046 514

(51) Int. Cl.
*A61B 6/00* (2006.01)
(52) U.S. Cl. ............................ 378/5; 382/128; 382/130
(58) Field of Classification Search .................. 378/4, 5, 378/8, 98, 98.11, 98.12
See application file for complete search history.

(56) References Cited

U.S. PATENT DOCUMENTS

| | | | |
|---|---|---|---|
| 3,848,130 A * | 11/1974 | Macovski | 378/98.9 |
| 3,965,358 A * | 6/1976 | Macovski | 378/5 |
| 3,974,386 A * | 8/1976 | Mistretta et al. | 378/98.11 |
| 4,463,375 A * | 7/1984 | Macovski | 378/98.12 |

(Continued)

FOREIGN PATENT DOCUMENTS

DE     102006009222 A1     9/2007

OTHER PUBLICATIONS

R.E. Alvarez and A. Macovski; "Energy-selective Reconstructions in X-ray Computerized Tomography", R.E. Alvarez and A. Macovski, Phys. Med. Biol., 1976, vol. 21, No. 5, 733-744,; Phys. Med. Biol., 1976, vol. 21, No. 5, pp. 733-744,; Others.

(Continued)

*Primary Examiner* — Edward Glick
*Assistant Examiner* — Alexander H Taningco
(74) *Attorney, Agent, or Firm* — Harness, Dickey & Pierce, P.L.C.

(57) ABSTRACT

A method and an image evaluation unit are disclosed for recognizing and marking contrast agents in blood vessels of the lung with the aid of a CT examination using at least two different x-ray energy spectra. In at least one embodiment, the method includes scanning a patient at least in the region of the lung with two different x-ray energy spectra, with the patient having contrast agents in the blood stream; reconstructing an at least two or three dimensional tomographic display for each x-ray energy spectrum which reproduces the local spectrum-specific absorption properties of the scanned region, wherein a surrounding area is defined for a multiplicity of voxels for which an average ratio is calculated with the aid of the local absorption values of the at least two x-ray energy spectra, which surrounding area specifies a measure for the ratio of the proportion of contrast agent to the proportion of soft tissue in the surrounding area of the respectively considered voxel, and wherein, in the case of this ratio dropping below a threshold value, this voxel is considered to have reduced circulation and is marked in a tomographic display.

19 Claims, 4 Drawing Sheets

U.S. PATENT DOCUMENTS

| | | | | |
|---|---|---|---|---|
| 5,396,418 | A | * | 3/1995 | Heuscher ........................ 378/15 |
| 5,687,208 | A | * | 11/1997 | Bae et al. ......................... 378/8 |
| 5,881,124 | A | * | 3/1999 | Giger et al. ...................... 378/8 |
| 6,301,498 | B1 | * | 10/2001 | Greenberg et al. ........... 600/425 |
| 6,438,403 | B1 | * | 8/2002 | Cline et al. .................... 600/410 |
| 6,442,235 | B2 | * | 8/2002 | Koppe et al. ................... 378/62 |
| 6,496,560 | B1 | * | 12/2002 | Lin et al. ........................ 378/62 |
| 6,512,807 | B1 | * | 1/2003 | Pohlman et al. .................. 378/4 |
| 7,778,454 | B2 | * | 8/2010 | Grasruck et al. ............. 382/128 |
| 2003/0040669 | A1 | * | 2/2003 | Grass et al. ................... 600/407 |
| 2004/0101089 | A1 | | 5/2004 | Karau |
| 2006/0050840 | A1 | * | 3/2006 | Ikeda et al. ...................... 378/8 |
| 2006/0134000 | A1 | * | 6/2006 | Heismann ...................... 424/9.4 |
| 2007/0217570 | A1 | | 9/2007 | Grasruck et al. |

OTHER PUBLICATIONS

W. Kalender et al. Digitale Bilddiagn. 7 (1987) pp. 66-72. Georg Thieme Verlag Stuttgart New York; Others.

* cited by examiner

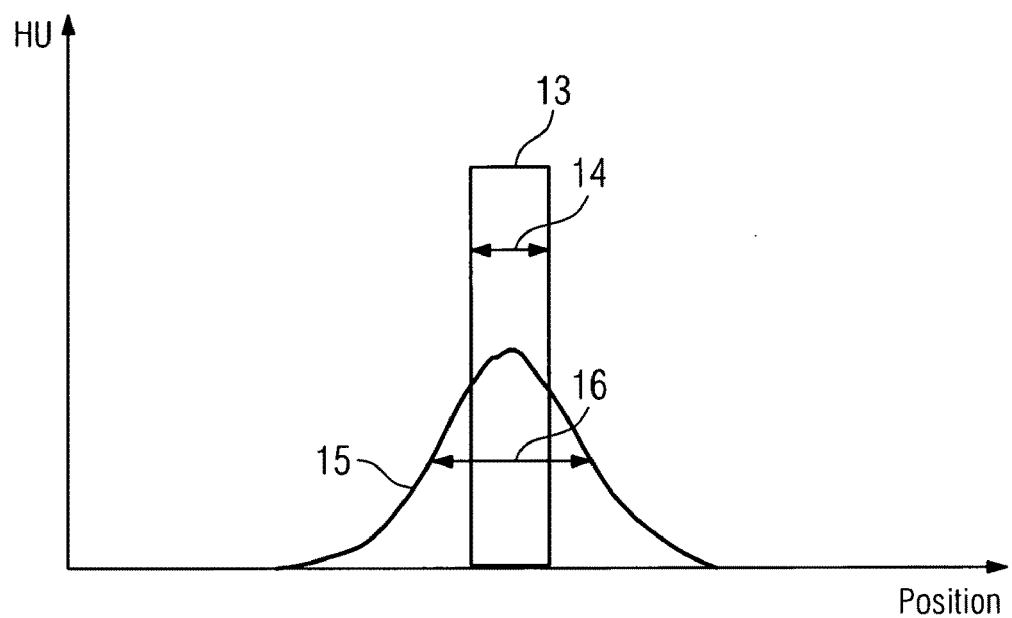
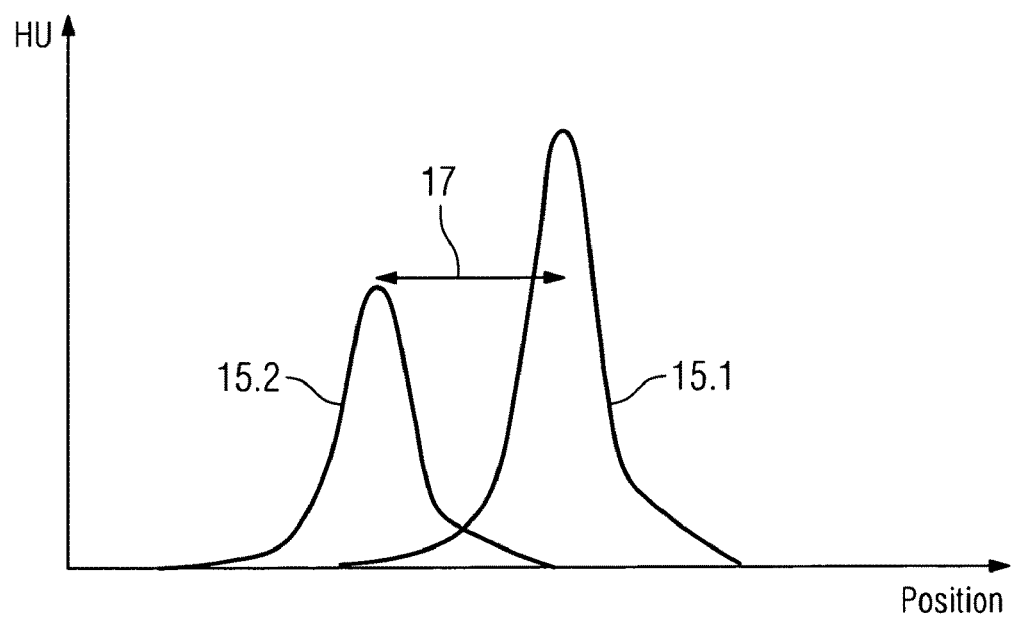

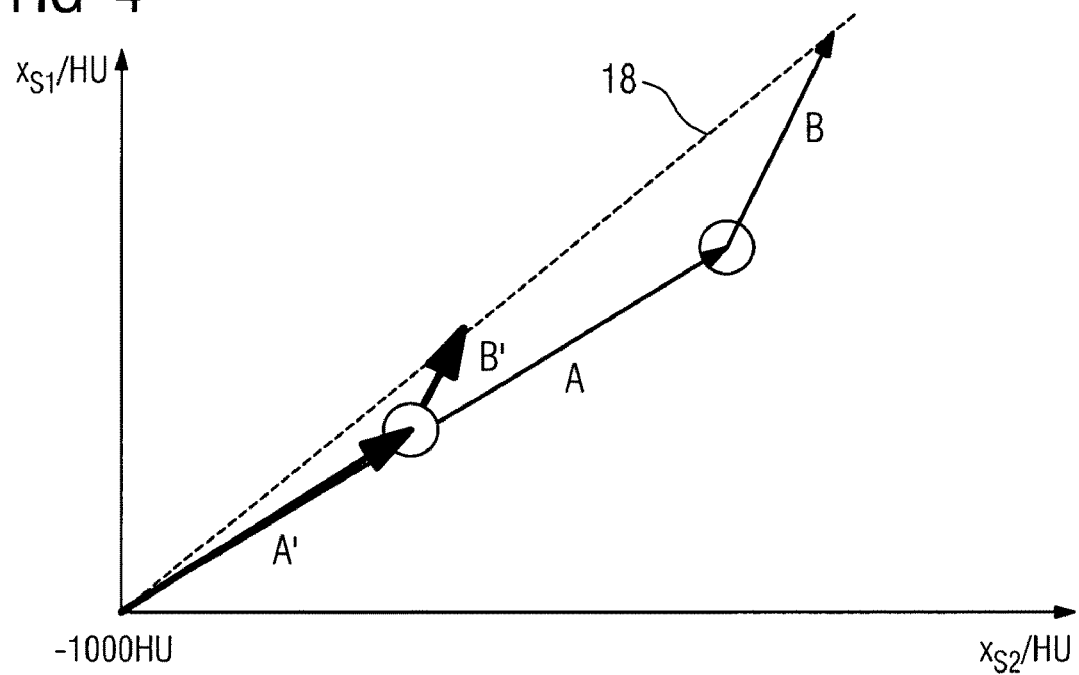
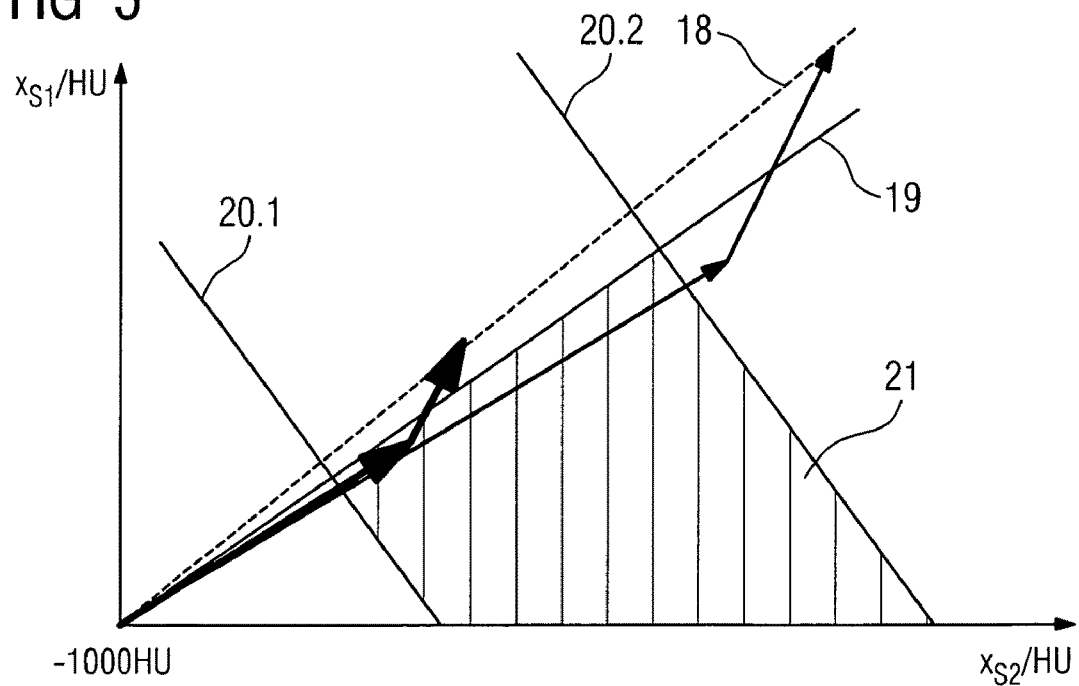

METHOD FOR RECOGNIZING AND MARKING CONTRAST AGENTS IN BLOOD VESSELS OF THE LUNG WITH THE AID OF A CT EXAMINATION AND AN IMAGE EVALUATION UNIT OF A CT SYSTEM

PRIORITY STATEMENT

The present application hereby claims priority under 35 U.S.C. §119 on German patent application number DE 10 2007 046 514.0 filed Sep. 28, 2007, the entire contents of which is hereby incorporated herein by reference.

FIELD

Embodiments of the invention generally relate to a method for recognizing and marking contrast agents in blood vessels of the lung with the aid of a CT examination using at least two different x-ray energy spectra, and/or to an evaluation unit of a CT system, with a patient being scanned at least in the region of the lungs with two different x-ray energy spectra, while the patient has contrast agents in the blood stream, and an at least two or three dimensional tomographic display being reconstructed which reproduces the local absorption properties of the scanned region.

BACKGROUND

By way of example, a method is described in the patent application US 2004/0101089 A1, the entire contents of which are hereby incorporated herein by reference.

When examining lung tissue, it is sometimes medically necessary to also evaluate the circulatory state of thin blood vessels. Due to partial volume effects, this evaluation is difficult using reconstructed CT images which display HU values, especially in the case of fine lung vessels. The HU values in the interior of the vessel calculated in the process depend inter alia on the vessel diameter, the reconstruction kernel and, if applicable, also on the slice thickness of the reconstructed slice images.

If the vessels are very thin, partial volume effects prevent a clear display of vessels supplied with contrast agent. In this case, these partial volume effects have effective diameters which can be significantly larger than the pixel diameter or voxel diameter of a CT image.

SUMMARY

In at least one embodiment of the invention, a method permits automated determination of the circulatory state of blood vessels in the lung tissue and displays it.

In at least one embodiment, the inventor has recognized the following:

In the case of CT images, which are recorded using a single x-ray spectrum, it is a problem in fine lung vessels that, due to the finite image focus, the HU value expected for blood is not measured in the center of the vessel because the adjacent air lowers this HU value. For this reason it is not possible to read-out whether or not the vessel contains contrast agent in addition to blood, using the HU value in the center of it.

Although scanning an examination object using a plurality of x-ray energy spectra—different technical methods are generally known to this end—cannot resolve the problem of the finite image focus, it is however possible to determine the ratio of the quantity of the contrast agent to the quantity of tissue within the same volume and use this to characterize the circulatory state. For a fixed contrast agent concentration in the blood, this ratio is independent of the size of the considered volume and the actual size of the vessel contained therein, provided that the vessel walls are disregarded. Large ratios characterize normal circulation; values in the vicinity of zero characterize circulatory disorders.

To calculate this ratio with the aid of tomographic images of a "dual energy" CT system, a two or three dimensional surrounding area can first of all be determined for each voxel. In principle, this surrounding area can have an arbitrary shape, but a convex shape lends itself to this purpose. As an additional criterion, it is possible to regard only voxels in the surrounding area whose arbitrarily linearly weighted HU value from the HU value of a first low energy radiation spectrum $x_{s1}$ and the HU value of a second, higher energy radiation spectrum $x_{s2}$ exceeds and/or drops below a certain threshold, where $x=ax_{s1}+bx_{s2}+c$. Coefficients a, b and c can be chosen arbitrarily. However, in the following text it is assumed for the purposes of simplification that, for the HU value x', $b=1-a$, and $c=0$.

A lower threshold for x' is expedient, because for low values of x', that is to say for voxels in the lung parenchyma, the contrast/noise ratio is significantly poorer than for voxels in the region of the vessel. Additionally, constant systematic errors in the subsequent processing have, relatively speaking, a more pronounced effect on low HU values than high HU values. Advantageously, this threshold can be set to be just above typical CT values for the parenchyma including contrast agents.

An upper threshold for x' can be used to remove calcium or metallic foreign bodies, for example, from the analysis.

The ratios which determine the circulatory state in the lung vessels considered can now be determined for the remaining voxels in various ways. In principle it is possible to use different methods for this, but these methods describe the same fundamental idea. The ratios are each designated $R_i$, with each index referring to a particular method of calculation:

1) Applying a generally known two-material decomposition from two CT images with respectively different energy spectra into equivalent densities of soft tissue $z_G$ and contrast agent $z_I$, and subsequently calculating the ratio $R_1=z_I/z_G$.

2) Carrying out a three-material decomposition from two CT images with respectively different energy spectra into material components of soft tissue $f_G$, contrast agent c and air. In the process, the ratio $R_2=c/f_G$ can be calculated from the material components, or the ratio $R_3$ can be formed by $$R_3 = \frac{x_I}{x_{vn} + 1000HU}$$

with the aid of a determined contrast agent image $x_I$ and a virtual native image $x_{vn}$.

3) Forming a ratio from the absorption coefficients $\mu_{s1}$ and $\mu_{s2}$ determined using the radiation spectra S1 and S2 by calculating $$R_4 = \frac{\mu_{s1}}{\mu_{s2}}$$

or by directly calculating the ratio from the corresponding HU values by calculating $$R_5 = \frac{x_{S1} + 1000HU}{x_{S2} + 1000HU}.$$

As an alternative to this, it is also possible to firstly calculate the ratio for every voxel in the selected surrounding area and subsequently carry out an averaging process. A further alternative is to generate images of the equivalent densities of the soft tissue and contrast agent with the aid of a raw-data based material decomposition, as is described, for example, in "Energy-selective Reconstructions in X-ray Computerized Tomography", R. E. Alvarez and A. Macovski, Phys. Med. Biol., 1976, Vol. 21, No. 5, 733-744, the entire contents of which are hereby incorporated herein by reference.

Subsequently, it is possible in turn to calculate the ratio from the averages of the equivalent densities over a surrounding area or individually for each voxel in the surrounding area, and then average over all voxels.

A threshold can then be selected for the ratio, with all values above this threshold being evaluated as characteristic of a healthy circulation. All values below the threshold are evaluated as having reduced circulation. The vessels with proper circulation can subsequently be marked on a CT image.

Furthermore, the ratio can be superposed onto the normal CT image or a suitable mixed image and be color-coded.

Hence, the method according to at least one embodiment of the invention can be structured into the following individual steps:
1) First of all, each voxel is checked as to whether a predetermined HU value range is adhered to in one of the two CT images reconstructed using the energy spectra S1 or S2, or in a weighted mixed image of these CT images. If this is not the case, this voxel is not evaluated any further. The HU value range can be chosen such that it is achieved only by vessels having a certain minimum size. This excludes very fine vessels for which the ratios cannot be determined with sufficient significance.
2) A surrounding area is defined for each selected voxel such that noise, vessel diameter and possible spatial offset between CT images have the smallest possible effect on the evaluation.
3) An average ratio is formed for this surrounding area and represents a measure of the ratio of the proportion of contrast agent to the proportion of soft tissue.
4) If this ratio exceeds a predetermined threshold, the voxel is considered to have normal circulation; if the ratio drops below the threshold, the voxel is considered to have reduced circulation.
5) A graphical display is output of at least one CT image with markings of the voxels considered to have reduced circulation; this is preferably a superposition of at least one colored mask or a color-coded display of the voxel-by-voxel ratios.

According to at least one of abovementioned ideas of at least one embodiment of the invention, the inventor proposes in the most general form a method for recognizing and marking blood vessels of the lung with the aid of a CT examination using at least two different x-ray energy spectra, comprising at least the following method steps:

scanning a patient at least in the region of the lung with two different x-ray energy spectra, with the patient having contrast agents in the blood stream, reconstructing an at least two or three dimensional tomographic display for each x-ray energy spectrum which reproduces the local spectrum-specific absorption properties of the scanned region, a surrounding area is defined for which for a multiplicity of voxels an average ratio is calculated with the aid of the local absorption values of the at least two x-ray energy spectra, which surrounding area indicates a measure of the ratio of the proportion of contrast agent to the proportion of soft tissue in the surrounding area of the respectively considered voxel, in the case of this ratio dropping below a predetermined threshold value this voxel is considered to have reduced circulation and is marked in a tomographic display.

Advantageously, the average ratio can be formed by the local absorption values of the at least two x-ray energy spectra. In this case, the ratio can be calculated as the quotient of the absorption coefficients determined from the two x-ray energy spectra $$R_4 = \frac{\mu_{S1}}{\mu_{S2}},$$

or as the quotient of the HU values determined from the two X-ray energy spectra $$R_5 = \frac{x_{S1} + 1000HU}{x_{S2} + 1000HU}.$$

In another embodiment of the method according to the invention, it is proposed that the scanned region's material is decomposed into two different materials, and two tomographic data records with local equivalent densities of each of the two different materials are determined, as described for example in Kalender W, Bautz W, Felsenberg D, Süß C, Klotz E, "Materialselektive Bildgebung und Dichtemessung mit der Zwei-Spektren-Methode I. Grundlagen und Methodik" [Material-selective imaging and density measurements using the two-spectra method I. Theory and methodology], Digitale Bilddiagn. 1987 June; 7(2):66-72 (the entire contents of which are hereby incorporated herein by reference), and that the average ratio is formed from the local equivalent densities of the two materials using $R_1 = z_I/z_G$.

As an alternative, it is also possible to decompose the material the scanned region into three different materials, as is described in an example manner in the patent application with the reference number DE 10 2006 009 222.8 (the entire contents of which are hereby incorporated herein by reference), by determining at least one tomographic virtual native image and a tomographic contrast agent image, with the average ratio in this case being formed from the tomographic virtual native image and the tomographic contrast agent image. In this case, the ratio $R_2 = c/f_G$ can be calculated as the quotient of the equivalent density values c of the contrast agent image and the equivalent density values $f_G$ of the virtual native image. It is likewise also possible to calculate the ratio using $$R_3 = \frac{x_I}{x_{vn} + 1000HU},$$

with $x_I$ being the voxel values of the contrast agent image and $x_{vn}$ being the voxel values of the virtual native image.

In order to reduce the computational complexity and speed up the method, it is possible for the image region in which further calculations are carried out to be limited in a particularly advantageous variant of the method before calculating the ratios by calculating a linearly weighted absorption value $x = a*x_{s1} + b*x_{s2} + c$ for each voxel of the scanned region using the CT image data $x_{s1}$ and $x_{s2}$ which was scanned with the two x-ray energy spectra S1 and S2 and reconstructed, and by checking whether a preset boundary value of the absorption value is exceeded. The rest of the method is carried out only on those voxels which exceed this bound. It should be mentioned in this regard that it is also within the scope of the invention to set the weighting factors a or b and the constant c to zero, that is to say that only the image data obtained by one of the two radiation spectra is checked for the bounds as described above.

In place of a lower bound, it is also possible to use a bounded range with an upper and lower bound by determining a linearly weighted absorption value for each voxel of the scanned region from the CT image data of the two x-ray energy spectra, and by checking whether a predetermined bounded range for the absorption value is adhered to, with the method being carried out only for those voxels which lie in this bounded range.

It is also advantageous if the defined surrounding area of a voxel comprises a preset radius r. The preset radius r can in this case be selected as a function of an observed vessel diameter and/or the image noise occurring and/or possible motion unsharpness, with the preset radius r increasing with increasing vessel diameter, increasing noise and/or increasing offset or increasing movement between the CT images recorded using the different spectra.

Furthermore, the marked voxels can be output in color.

An image evaluation unit for a CT system comprising a processor and a program memory, with the program memory comprising a program code which executes the method according to at least one embodiment of the invention when the evaluation unit is operating, is also included within the scope of at least one embodiment of the invention.

BRIEF DESCRIPTION OF THE DRAWINGS

In the following text, embodiments of the invention are described in more detail with the aid of the figures, in which only features which are necessary for understanding the embodiments of invention are illustrated. In this case, the following reference symbols are used: 1: dual energy CT system; 2: first x-ray tube for the first spectrum; 3: first detector; 4: second x-ray tube for the second spectrum; 5: second detector; 6: gantry housing; 7: patient; 8: displaceable patient couch; 9: system axis; 10: image evaluation unit; 11: CT slice image created using the first energy spectrum; 12: CT slice image created using the second energy spectrum; 13: ideal HU value profile of a vessel; 14: actual diameter of a vessel; 15: measured HU value profile of a vessel; 15.1: HU value profile of a vessel measured using the first energy spectrum; 15.2: HU value profile of a vessel measured using the second energy spectrum; 16: apparent vessel diameter; 17: spatial offset; 18: position of the voxels of a lung without contrast agents in the HU value diagram; 19: boundary line; 20.1: lower bound; 20.2: upper bound; 21: region of voxels with reduced circulation; A, A', B, B': vectors in the HU value diagram; c: equivalent density value of the contrast agent; $f_G$: equivalent density value of the virtual native image; $Prg_1$-$Prg_n$: computer programs, $R_i$: ratios of contrast agent quantity and tissue quantity; S1, S2: x-ray energy spectra; $x_{s1}$, $x_{s2}$: spectrum-specific absorption values in HU (=Hounsfield Units); $x_{vm}$: absorption values of the native image in HU; $x_f$: absorption values of the contrast agent image in HU; $z_G$: equivalent density of the tissue; $z_f$: equivalent density of the contrast agent: $z_1$, $z_2$: equivalent densities; $\mu_{s1}$, $\mu_{s2}$: absorption coefficients.

In more detail:

FIG. 2 shows the HU value profile across a vessel subject to the partial volume effect;

FIG. 3 shows the HU value profile across a vessel using two energy spectra, the scan of the profile being subject to the partial volume effect and movement offset;

FIG. 4 shows in illustration in the form of a graph the pixel-by-pixel HU value combinations from two CT images of a lung, recorded using differing energy spectra;

FIG. 5 shows an illustration of the method according to the invention for determining ratios on the basis of the graph of FIG. 4;

DETAILED DESCRIPTION OF THE EXAMPLE EMBODIMENTS

Figure 1:
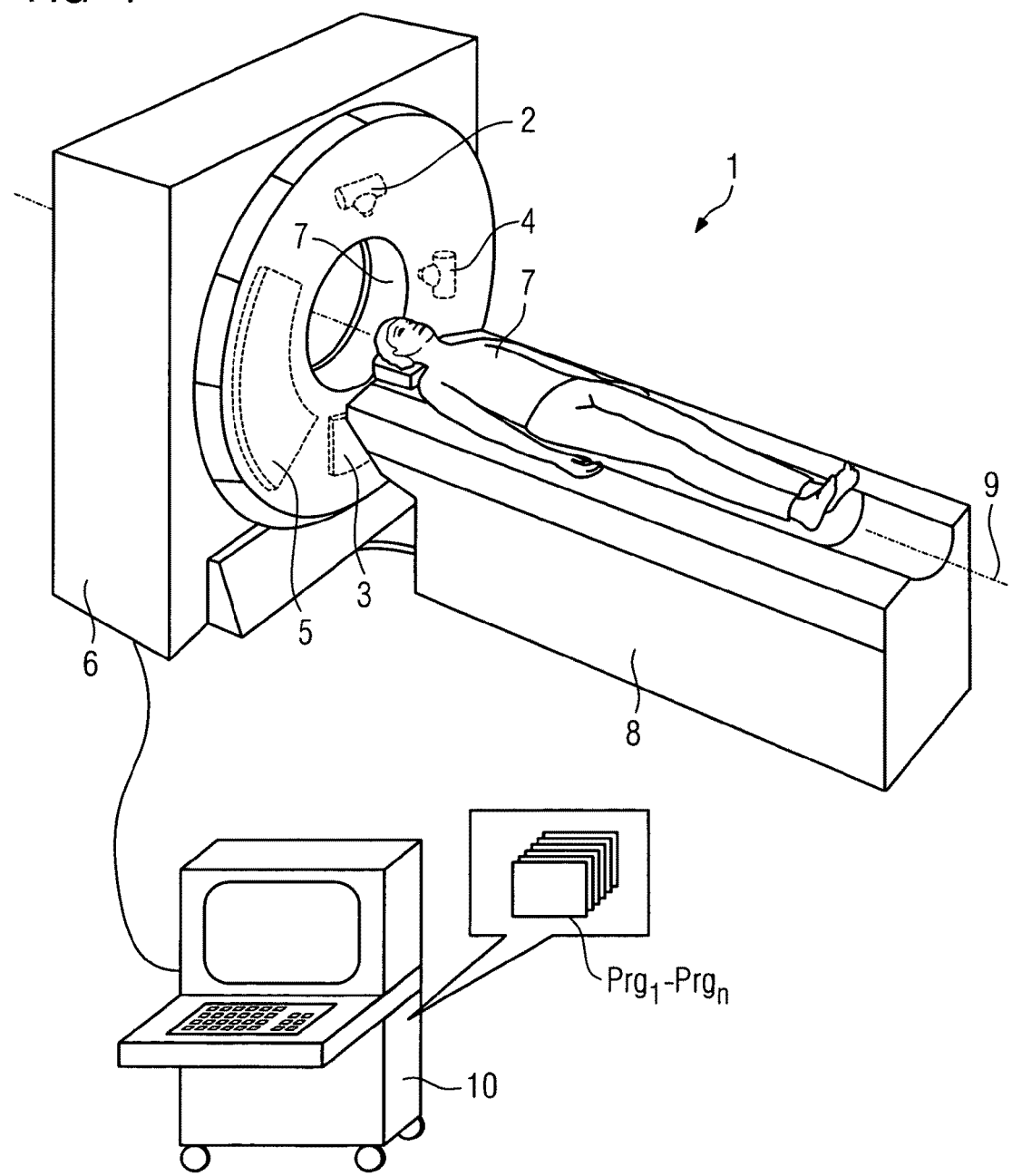
FIG. 1 shows a dual energy CT system with an image evaluation unit for carrying out the method according to an embodiment of the invention.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 shows, in an example embodiment, a dual energy CT system 1 which can carry out the method according to an embodiment of the invention for recognizing and marking blood vessels of the lung using at least two CT images with differing x-ray energy spectra. For this purpose, two x-ray tubes 2 and 4 with respectively opposing detector systems 3 and 5 are located on a gantry in the gantry housing 6, by means of which a patient 7 can be scanned simultaneously using two differing x-ray energies. For this purpose, the patient 7 lying on a patient couch 8 is pushed through a measurement field between the x-ray tubes 2, 4 and the detectors 3, 5 along the system axis 9, while the attenuation of the x-ray radiation with differing energy spectra emitted by the x-ray tubes is determined with the aid of detectors. With the aid of the evaluation unit 10 and some of the computer programs $Prg_1$-$Prg_n$ executed therein, the absorption data obtained is used to reconstruct tomographic image data records, for example slice images or 3D volume data records, which reproduce the local and energy spectrum-specific absorption values.

Of course, the type of scanning described here does not constitute a limitation of the method according to an embodiment of the invention. Thus, it is known to a person skilled in the art that it is also possible to obtain energy-specific tomographic images of an examination object using different methods and differently constructed CT systems. Hence, it is also possible to operate a CT system with a single x-ray tube alternately with different radiation spectra, or an energy-resolving detector can be used when scanning with a single spectrum. It is essential to the invention only that eventually CT images of the same object with two energy specific absorption data records are available for processing.

Figure 6:
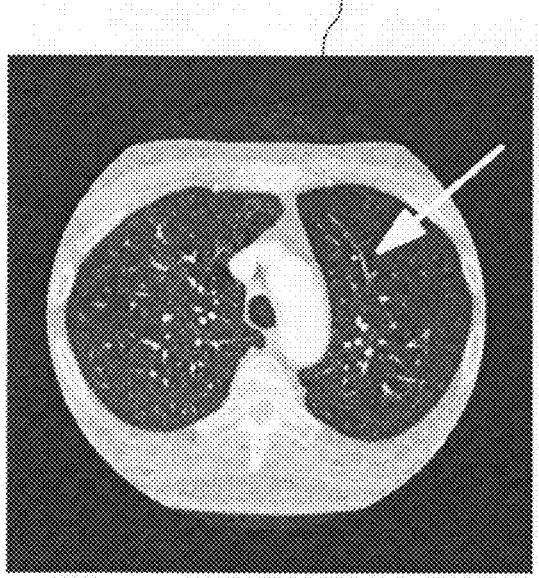
FIG. 6 shows a conventional contrast agent enhanced CT image of the region of the thorax including the lung, recorded using a first x-ray energy spectrum.
Figure 7:
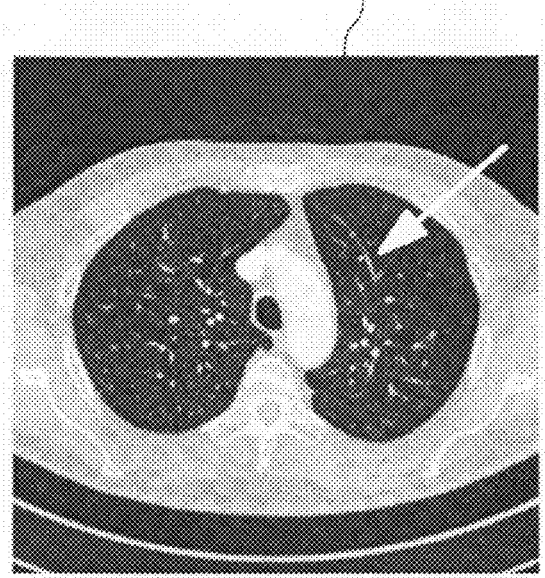
FIG. 7 shows a conventional contrast agent enhanced CT image of the region of the thorax including the lung, recorded using a second x-ray energy spectrum

FIGS. 6 and 7 show, in an example manner, two CT slice images 11 and 12 from the region of the thorax of a patient, generated using two different x-ray energy spectra—using 80 kV acceleration voltage for image 11 and 140 kV acceleration voltage for image 12. It is inherent to the system that the measurement field in image 11 is smaller than the measurement field in image 12. A common diagnostic problem is to recognize stenoses or reduced circulation in thin vessels of the lung in such image material, in order to recognize emboli present or to prevent the setting-in of embolism.

Due to the peculiarities of the measurement method in computed tomography and of the reconstruction method, it is known that partial volume effects occur when displaying small structures, that is to say also when displaying thin vessels in the lung, which additionally complicate recognizing the circulatory state of small vessels. This is substantially due to the limited resolution of the CT and the noise due to applying the lowest dosage possible in the scan.

FIG. 2 shows the effect of the partial volume effect on the basis of the HU value profile across a small vessel. The measured HU value, a measure of the local absorption, is plotted on the ordinate of the illustrated graph, while the abscissa shows the position along a slice across a vessel with the diameter 14. The curve 13 shows the idealized HU value profile which should ideally occur when passing through a vessel slice during the absorption measurement. However, due to the partial volume effect, the actually measured HU values corresponding to the line 15 are flattened and widened. This results in the diameter 16 of the vessel displayed in the CT image appearing to be wider than it actually is and the image appears less focused, resulting in good diagnosis becoming more difficult.

When evaluating two CT images recorded at different times, there is an additional problem due to the fact that it is impossible to avoid movements between the records and thus the respectively congruent voxels do not reproduce the identical location in a displayed organ when comparing two CT images of the same object.

FIG. 3 clarifies this on the basis of two HU value profiles 15.1 and 15.2 across the same vessel, recorded at different times and with different energy spectra. In this case, the abscissa and ordinate correspond to the illustration in FIG. 2. There is an offset by a distance 17 of the vessel considered due to a movement of the patient between or during the recordings. If such records are simply to be compared to one another voxel-by-voxel, this would result in drastic HU value differences which would lead to false ratios. Due to this, it is thus necessary to take into account a possible offset due to movements occurring (which are relatively small). By way of example, this can be achieved by considering the average in a fairly large surrounding area around a voxel. The surrounding area considered should in this case be smaller than the typical separation between the vessels of diagnostic interest, that is to say <5 cm. It is expedient to mutually register the CT images before comparing them, if the offset is relatively large.

The definition of the ratio, which is a measure of the ratio of the proportion of contrast agent to the proportion of soft tissue in the surrounding area of the respectively considered voxel, will be explained now on the basis of FIGS. 4 and 5. On these graphs, the HU values $x_{s1}$ and $x_{s2}$ of the same voxel of two CT images recorded with radiation spectra S1 and S2 are plotted on the ordinate and the abscissa. The radiation spectrum S1 in this case has a lower average energy than the radiation spectrum S2. The point of intersection of ordinate and abscissa corresponds to the HU values $x_{s1} = x_{s2} = -1000\text{HU}$.

In a perfused lung, the blood contains dissolved iodine with a constant concentration. The magnitude of the vector B, which represents the absorption properties of iodine, is directly proportional to the magnitude of the vector A, which corresponds to the absorption of blood, and thus:

$$|B| = k|A|$$

Independent of how much air is now contained in a considered surrounding area, the proportion of iodine B' and proportion of blood A' of the total absorption also satisfy:

$$|B'| = k|A'|$$

Hence all voxels in the lung lie on the dashed line 18.

On this graph, the partial volume effect is indicated by the shortening of the vector A to A', and the shortening of vector B to B'. The circles show the position of the lung tissue without a contrast agent.

If the iodine concentration is lower in one region of the lung, all voxels there lie on a line through the point of intersection of ordinate and abscissa at (−1000,−1000), the gradient of which line is less than the gradient of the line 18.

This means that a limiting concentration is represented by a boundary line through the point (−1000,−1000). All voxels above this line have normal circulation. All voxels below the line have reduced circulation.

FIG. 5 once again in the form of a graph, shows an optimum selection or comparison method according to the invention based on two CT image data recorded with two differing spectra.

When considering the images, all voxels located outside the area of the boundary lines 20.1 and 20.1 are rejected first. Subsequently, the voxels whose ratio lies above the boundary line 19 are rejected, and the remaining voxels belonging to the shaded region 21 are considered to be voxels characterizing a vessel with reduced circulation.

According to an embodiment of the invention, it is now possible to use different variables to determine whether a voxel lies above or below the boundary line:

Ratio of the equivalent densities $z_I$ and $z_G$ from a 2 material decomposition Ratio $x_I/(x_{vn}+1000\text{HU})$ from a 3 material decomposition Gradient $(x_{80}+1000\text{HU})/(x_{140}+1000\text{HU})$ relative to the point (−1000,−1000)

A bound can be determined for all three variables, below which the considered region lies below the boundary line in the diagram.

Figure 8:
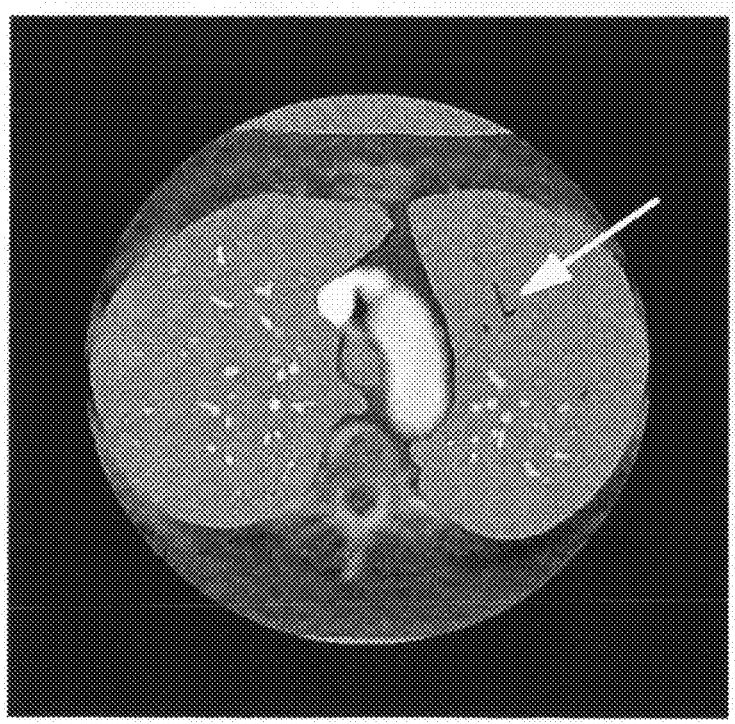
FIG. 8 shows an evaluation of the CT images from FIGS. 6 and 7 according to an embodiment of the invention by forming ratios.

If the method above, of an embodiment of the invention, is applied to the two CT images in FIGS. 6 and 7, this results in an illustration of ratios as shown in FIG. 8. The arrow in FIGS. 6 to 8 points to a vessel which was recognized as having reduced circulation as a result of the method according to an embodiment of the invention and which indicates the presence of an embolism. In addition, such vessels can be highlighted by a colored display, or it is possible to keep the familiar impression of a CT image with markings, preferably color-coded ratios, by superposing these regions illustrated in color on a normal CT image from FIG. 6 or 7.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for recognizing and marking blood vessels of a lung with the aid of a CT examination using at least two different x-ray energy spectra, the method comprising:

scanning a patient, at least in a region of the lung, with two different x-ray energy spectra, with the patient having only a single contrast agent administered; and reconstructing an at least two dimensional tomographic image for each x-ray energy spectrum which reproduces local spectrum-specific absorption properties of the scanned region, wherein a surrounding area is defined for a multiplicity of voxels for which an average ratio is calculated with the aid of local absorption values of the at least two x-ray energy spectra, the average ratio representing a measure for a ratio of a proportion of the single contrast agent to a proportion of soft tissue in the surrounding area of the respectively considered voxel, and upon the average ratio dropping below a threshold value, the respectively considered voxel is considered to have reduced blood circulation and is marked in the reconstructing at least two dimensional tomographic image.

2. The method as claimed in claim 1, wherein the average ratio is formed by local absorption values of the at least two x-ray energy spectra.

3. The method as claimed in claim 2, wherein a quotient of absorption coefficients determined by two x-ray energy spectra, respectively, is used as the average ratio.

4. The method as claimed in claim 2, wherein a quotient of HU values determined by two x-ray energy spectra, respectively, is used as the average ratio.

5. The method as claimed in claim 1, wherein:
material of the scanned region is decomposed for two different materials and two tomographic data records with equivalent densities of each of the two different materials are determined, and
a quotient of the equivalent densities of the two materials, respectively, determined by two x-ray energy spectra is used as the average ratio.

6. The method as claimed in claim 1, wherein:
material of the scanned region is decomposed into soft tissue and air on one hand, and the single contrast agent on the other, and at least one tomographic virtual native image, which displays the soft tissue and the air, and a tomographic contrast agent image, which displays the single contrast agent, are determined, and
the average ratio is formed with the aid of the tomographic virtual native image and the tomographic contrast agent image.

7. The method as claimed in claim 6, wherein the average ratio is based on the local absorption values of the contrast agent image $X_I$ and of the local absorption values of the virtual native image $X_{V_n}$ using the formula $$R_3 = \frac{x_I}{x_{vn} + 1000HU},$$

wherein R3 is the average ratio.

8. The method as claimed in claim 6, wherein a quotient of equivalent density values of the contrast agent image and equivalent density values of the virtual native image is used as the average ratio.

9. The method as claimed in claim 1, wherein a linearly weighted absorption value is determined from reconstructed image data of the two x-ray energy spectra for each voxel of the scanned region before carrying out the defining of the surrounding area and the marking, wherein if a threshold value for a linearly weighted absorption value is exceeded and the method is carried out only for those voxels which exceed this threshold value.

10. The method as claimed in claim 1, wherein a linearly weighted absorption value is determined from reconstructed image data of the at least two x-ray energy spectra for each voxel of the scanned region before carrying out the defining of the surrounding area and the marking, wherein if a bounded range for the linearly weighted absorption value is adhered to and the method is carried out only for those voxels which lie in this bounded range.

11. The method as claimed in claim 1, wherein the defined surrounding area of a voxel comprises a preset radius.

12. The method as claimed in claim 11, wherein the preset radius is selected as a function of at least one of an observed vessel diameter, image noise occurring and possible motion unsharpness, with the preset radius increasing with increasing vessel diameter and increasing noise.

13. The method as claimed in claim 1, wherein the marked voxels are displayed in color.

14. The method of claim 1, wherein the average ratio is calculated through direct use of the local absorption values of the at least two x-ray energy spectra.

15. An image evaluation unit for a CT system comprising:
a processor; and
a program memory, the program memory including a program code where, after a scan of a patient, using the CT system, of at least the region of a lung with two different x-ray energy spectra, with the patient having only a single contrast agent administered, the program code executes the following when the image evaluation unit is operating:
reconstructing an at least two dimensional tomographic image for each x-ray energy spectrum which reproduces local spectrum-specific absorption properties of the scanned region;
defining a surrounding area for a multiplicity of voxels for which an average ratio is calculated with the aid of local absorption values of the at least two x-ray energy spectra, the average ratio representing a measure for a ratio of a proportion of the single contrast agent to a proportion of soft tissue in the surrounding area of the respectively considered voxel; and
displaying a tomographic display of the scanned region, with voxels being considered to have reduced blood circulation and marked as soon as the average ratio drops below a threshold value.

16. The image evaluation unit as claimed in claim 15, wherein the average ratio is formed by local absorption values of the at least two x-ray energy spectra.

17. A non-transitory tangible computer readable medium including program segments for, when executed on a computer device, causing the computer device to implement the method of claim 1.

18. A method for recognizing and marking blood vessels of the lung with the aid of a CT examination using at least two different x-ray energy spectra, the method comprising:
scanning a patient, at least in a region of the lung, with two different x-ray energy spectra, with the patient having only a single contrast agent administered;
reconstructing an at least two dimensional tomographic image for each x-ray energy spectrum which reproduces local spectrum-specific absorption properties of the scanned region;
defining a surrounding area for a multiplicity of voxels for which an average ratio is calculated with the aid of local absorption values of the at least two x-ray energy spectra, average ratio representing a measure for a ratio of a proportion of the single contrast agent to a proportion of soft tissue in the surrounding area of the respectively considered voxel; and
displaying a tomographic image of the scanned region, with voxels being considered to have reduced blood circulation and marked as soon as the average ratio drops below a threshold value.

19. A non-transitory tangible computer readable medium including program segments for, when executed on a computer device, causing the computer device to implement the method of claim 18.

* * * * *